United States Patent [19]

Sih et al.

[11] 4,447,620

[45] May 8, 1984

[54] IMIDAZOLYL-SUBSTITUTED BENZOTHIOPHENES

[75] Inventors: John C. Sih, Kalamazoo; Chiu-Hong Lin, Portage, both of Mich.

[73] Assignee: The Upjohn Company, Kalamazoo, Mich.

[21] Appl. No.: 433,941

[22] Filed: Oct. 12, 1982

Related U.S. Application Data

[63] Continuation-in-part of Ser. No. 385,619, Jun. 8, 1982, abandoned.

[51] Int. Cl.$^3$ ............................................ C07D 409/06
[52] U.S. Cl. ..................................... 548/336; 544/146; 544/376; 546/202; 548/525
[58] Field of Search ........................................ 548/336

[56] References Cited

U.S. PATENT DOCUMENTS 4,112,224 9/1978 Bundy ................................. 542/426
4,259,338 3/1981 Paioni et al. ........................ 424/267

FOREIGN PATENT DOCUMENTS 50957 5/1982 European Pat. Off. .
2537837 3/1976 Fed. Rep. of Germany .
2039903A 8/1980 United Kingdom .

OTHER PUBLICATIONS

D. Harris, et al., *Advances in Prostaglandin and Thromboxane Research*, 6:437 (1980).
T. Miyamoto, et al., *Advances in Prostaglandin and Thromboxane Research*, 6:443 (1980).
H. Tai, et al., *Advances in Prostaglandin and Thromboxane Research*, 6:447 (1980).

*Primary Examiner*—Richard A. Schwartz
*Attorney, Agent, or Firm*—Lawrence T. Welch

[57] ABSTRACT

The present invention provides novel imidazolyl-benzothiophenes and derivatives thereof which are useful as thromboxane A$_2$ (TXA$_2$) synthetase inhibitors and as such represent potent pharmacological agents.

2 Claims, No Drawings

IMIDAZOLYL-SUBSTITUTED BENZOTHIOPHENES

CROSS REFERENCE TO RELATED APPLICATIONS

This application is a continuation in part of application Ser. No. 385,619, filed June 8, 1982, now abandoned.

BACKGROUND OF THE INVENTION

The present invention relates to novel compositions of matter. More particularly, the present invention relates to imidazolyl-substituted benzothiophenes and derivatives thereof. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromoboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Thus, the present invention particularly provides:
A compound of the formula I wherein $Z_3$ is
(a) imidazolyl, or
(b) imidazolyl substituted by ($C_1$–$C_3$)alkyl;
wherein $X_3$ is
(a) —$(CH_2)_n$—,
(b) —CHOH—, or
(c) —C(O)—;
wherein $R_1$ is hydrogen, a pharmacologically acceptable cation, ($C_1$–$C_{12}$) alkyl, ($C_3$–$C_{10}$) cycloalkyl, ($C_7$–$C_{12}$) aralkyl, phenyl, phenyl mono-, di-, or trisubstituted by chloro, ($C_1$–$C_3$) alkyl, or phenyl para-substituted by
(a) —NHCO—$R_{25}$,
(b) —O—CO—$R_{26}$,
(c) —CO—$R_{24}$,
(d) —O—CO—(p—Ph)—$R_{27}$, or
(e) —CH=N—NH—CO—$NH_2$,
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein —(p—Ph) is 1,4-phenylene;
wherein $R_7$ is
(a) hydrogen,
(b) —$CH_2OH$,
(c) —$COOR_1$,
(d) —$CH_2N(R_4)_2$,
(e) —CN
(f) —$C(ON(R_4)_2$, or
(g) —C(O)—$R_4$;
wherein $R_4$ is
(a) hydrogen
(b) ($C_1$–$C_4$)alkyl, or
(c) phenyl;
wherein $R_9$ and $R_{12}$ are the same or different and are
(a) hydrogen,
(b) ($C_1$–$C_4$)alkyl
(c) fluoro,
(d) chloro,
(e) bromo,
(f) —$OCH_3$, or,
(g) when taken together and attached to contiguous carbon atoms, —O—$CH_2$—O—;
wherein D represents a single or a double bond; and
wherein m and n are the samethipo or different and are the integers 0 to 4, inclusive; including, pharmacologically acceptable acid addition salts thereof; and
when D represents a single bond, an enantiomer or a racemic mixture of enantiomers thereof.

The carbon atom content of various hydrocarbon-containing moieties is indicated by a prefix designating the minimum and maximum number of carbon atoms in the moiety, i.e., the prefix ($C_i$–$C_j$) indicates a moiety of the integer "i" to the integer "j" carbon atoms, inclusive. Thus ($C_1$–$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
 1-methylpiperidine,
 4-ethylmorpholine,
 1-isopropylpyrrolidine,
 2-methylpyrrolidine,
 1,4-dimethylpiperazine,
 2-methylpiperidine,
and the like, as well as amines containing water-solubilizing or hydrophilic groups, e.g.,
 mono-, di-, and triethanolamine,
 ethyldiethanolamine,
 N-butylethanolamine,
 2-amino-1-butanol,
 2-amino-2-ethyl-1,3-propanediol,
 2-amino-2-methyl-1-propanol,
 tris(hydroxymethyl)aminomethane,
 N-phenylethanolamine,
 N-(p-tert-amylphenyl)diethanolamine,
 glactamine,
 N-methylglycamine,
 N-methylglucosamine,
 ephedrine,
 phenylephrine,
 epinephrine,
 procaine,
and the like. Further useful amine salts are the basic amino acid salts, e.g.,
 lysine and
 arginine.

Examples of suitable pharmacologically acceptable quaternary ammonium cations are
 tetramethylammonium,
 tetraethylammonium,
 benzyltrimethylammonium,
 phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as benzofurans, using the Chemical Abstracts numbering system (see Naming and Indexing of Chemical Substances for Chemical Abstracts during the Ninth Collective Period (1972-1976), a reprint of section IV from the Volume 76 Index Guide.)

The compounds of the present invention are tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors are tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

The novel compounds of this invention are thus highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g to about 500 $\mu$g/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219:299 (1981).

The compounds of the present invention are prepared by the methods depicted in Charts A–G.

The benzothiophenes of the present invention are prepared by the method of Chart A. Conversion of the formula X thiophenol to the formula XII benzothiophene is accomplished using known methods as described, e.g., in Y. Matsuki, et al., Nippon Kugaku Zasshi 87:186 (1966) and Chapman, et al., J. Chem. Soc. 514 (1968). The formula XXII benzothiophene thus prepared is then carboxylated by known means (e.g., pouring a solution of this compound, in an inert solvent in the presence of n-butyllithium, over crushed dry ice) to yield the formula XIII product. The formula XIII compound is alkyl chlorinated by treatment with paraformaldehyde and zinc chloride to yield the formula XIV compound. The XVI compound is reacted with imidazole or an alkyl substituted imidazole to yield the formula XV product.

For compounds wherein m is one, the method of Chart B is used. An ester of the Formula XL ($R_{10}$ is all substituents within the scope of $R_1$ except the pharmacologically acceptable cations) is reduced with lithium aluminum hydride in ether or tetrahydrofuran to yield the corresponding alcohol after workup. This alcohol is tosylated or mesylated using p-toluenesulfonyl chloride or methanesulfonyl chloride in pyridine to yield the Formula XLII product. (Ts indicates the tosylated compound, but the compound could also be mesylated). This compound is treated with excess sodium cyanide in dimethylformamide (DMF) and stirred under nitrogen at room temperature for 5 hr to yield the Formula XLIII cyano compound. This compound is dissolved in ethanol and treated with 25% aqueous potassium hydroxide to yield the corresponding acid. This compound is esterified by means well known in the art, e.g., treatment with diazomethane in methanol for the methyl ester. Pharmacologically acceptable salts are also prepared by means well known in the art.

Chart C depicts the synthesis of compounds of the present invention wherein m is 2, 3, or 4. In Chart C, q is zero, one, or 2. An ester of the Formula L is reduced with diisobutylaluminum hydride (DIBAL) in toluene or methylene chloride at low temperature to yield, after workup, the Formula LI aldehyde. Reaction of this aldehyde with an alkoxy alkylene-triphenylphosphorane of the formula $Ph_3P=CHCH_2-(CH_2)_qCOOR_{10}$ (wherein Ph is phenyl) yields the unsaturated ester of the Formula LII after workup. Careful reduction of this unsaturated ester by reaction with one equivalent of hydrogen over palladium-on-carbon in alcohol yields the saturated ester of the Formula LIII. The free acid or a pharmacologically acceptable salt of this ester is prepared by means well known in the art. The corresponding amides, phenacyl esters, and the like are prepared by the methods depicted in e.g., U.S. Pat. Nos. 4,292,445 and 4,172,206.

The dihydrobenzothiophenes are prepared as depicted in Chart D. A solution of a formula LX benzofuran in water is stirred with excess sodium amalgam (NaHg) for 24 hr. After workup there is obtained the corresponding Formula LXI dihydrobenzothiophenes. (See, e.g., D. T. Witiak, et al., J. Med. Chem. 14, 754 (1971).)

Reduction of the corresponding acid or ester of the formula $COOR_{10}$ with lithium aluminum hydride as depicted in Chart B, (XL to XLI) is used to prepare all of the corresponding alcohols within the scope of Formula I. Conversion of the alcohol to a corresponding acid addition salt is accomplished by known means.

Substituted benzothiophenes (i.e. compounds wherein $R_9$ and $R_{12}$ are other than hydrogen) are prepared by the methods depicted in Charts E and F.

Chart E depicts a method for preparing methyl or methoxy substituted benzofurans or benzothiophenes. In Chart E, $R_{19}$ is methyl or methoxy. The formula CXV ether is hydrolyzed (using hydrobromic acid for example) to yield the formula CXVI alcohol. Similarly, the formula CXV' ether is hydrogenolyzed with hydrogen over palladium on carbon catalyst to yield the formula CXVI alcohol, which is converted to the thiophenol as described below and as depicted in Chart F. This compound is then converted to the compounds of this invention by the method of Chart A.

Chart F depicts a general method for preparing the substituted benzothiophenes of this invention. The $R_9$ and $R_{12}$ substituted paramethylthiophenol starting materials of the formula CXXXI are thus prepared by conversion of an appropriate formula CXXX substituted phenol into a thiophenol using the well established Newman-Kwart rearrangement (see, e.g., Org. Syn., 51:139 (1971)) and other related procedures. See also the Schönberg rearrangement by J. L. Wardell in "The Chemistry of the Thiol Group", ed. S. Patai, Wiley, New York, 1974, p. 163 and the Kawata-Harano-Taguchi rearrangement, Chem. Pharm. Bull. (Japan), 21, 604 (1973). The para-methylphenols are either commercially available or can be prepared by methods known in the art.

Similarly, various substituted hydroxy benzaldehydes are available commercially or may be prepared by methods known in the art. The hydroxybenzaldehydes are thus converted to the claimed benzothiophenes as described above.

Chart G depicts a method for preparing compounds wherein $X_3$ is —C(O)—. A compound of the formula CXX is treated with potassium superoxide to yield the formula CXXI compound.

Preparation of various other benzothiophene derivatives within the scope of this invention are prepared by analogous procedures well known in the art.

Certain compounds of the present invention are preferred. Thus, compounds of the formula I, wherein D denotes a double bond, $Z_3$ is imidazolyl, $X_3$ is —$(CH_2)_n$— (wherein n is zero or one, more preferably one), m is zero, $R_7$ is $COOR_1$, $R_1$ is Na or H, $R_9$ and $R_{12}$ are hydrogen, are preferred.

DESCRIPTION OF THE PREFERRED EMBODIMENTS

The present invention is seen more fully by the Examples given below.

PREPARATION 1

Methyl 5-chloromethyl-benzothiophene-2-carboxylate and

Methyl 4-chloromethyl-benzothiophene-2-carboxylate

Refer to Chart A (conversion of XIII to XIV).

A three-neck round-bottomed flask equipped with a magnetic stirring bar, a condenser, and a gas bubbler, is charged with a solution of methyl benzothiophene-2-carboxylate (XIII) (32.6 g, 0.17 mol) dissolved in 85 ml of chloroform. Paraformaldehyde (6.7 g, 0.22 mol) and zinc chloride (6.1 g, 0.045 mol) (dried at 100° C. under vacuum for 2 days) are addefd. The resulting mixture is heated to 50° C. and anhydrous hydrogen chloride gas is bubbled slowly through the magnetically stirred mixture. After 4–5 hr, the mixture is cooled, diluted with chloroform and washed with water, saturated aqueous sodium bicarbonate, and brine. Drying ($MgSo_4$), filtration, and concentration afford the crude product which is purified by chromatography to give the titled product.

EXAMPLE 1

Methyl 5-N-imidazolylmethyl-benzothiophene-2-carboxylate and Methyl 4-N-imidazolylmethylbenzothiophene-2-carboxylate A two-neck round-bottomed flask equipped with a magnetic stirring bar is charged with 0.264 g (5.5 mmol) of sodium hydride (50% active) under a nitrogen atmosphere. The hydride is washed twice with hexane and suspended in 10 ml of DMF. Imidazole (0.375 g, 5.5 mmol) dissolved in 2 ml of DMF is added dropwise over a period of 5 min. Gas evaluation starts immediately. The mixture is warmed to 90° C. with stirring for one hr. The yellow solution is then cooled to room temperature and a solution of 1.2 g (5.0 mmol) of methyl 5- (and 4-) chloromethyl benzothiophene-2-carboxylate in DMF is added dropwise over a period of 5 min. The mixture is stirred at room temperature for 40 min and quenched with brine. Extraction with ethyl acetate is followed by washing the organic layer with water and brine. Drying ($MgSO_4$), filtration and concentrations afford the crude product which is purified by chromatography to give the titled products.

EXAMPLE 2

2-Hydroxymethyl-5-N-imidazolylmethyl benzothiophene

Refer to Chart B (conversion of XL to XLI where $Z_3$ is imidazol, $X_3$ is —$CH_2$—, $R_2$ is H, and $R_{10}$ is —$CH_3$).

Methyl 5-N-imidazolylmethyl-benzothiophene-2-carboxylate is dissolved in THF. Two to four equivalents of lithium aluminum hydride under a nitrogen atmosphere. Work-up and purification afford the titled product.

4,447,620
TABLE I
FORMULAS
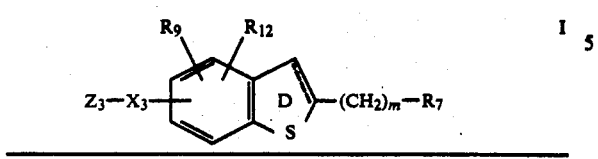  I
CHART A
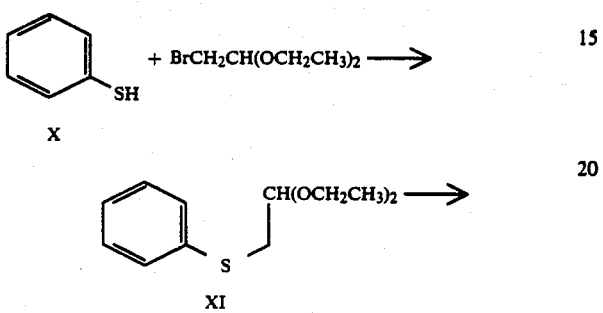
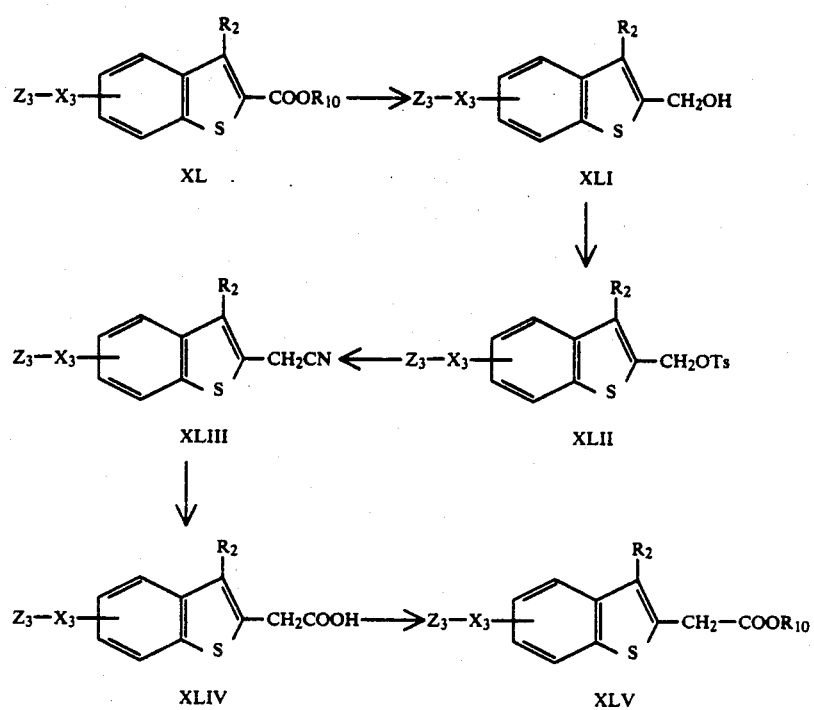
-continued
CHART A
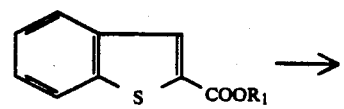  XIII
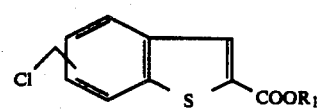  XIV
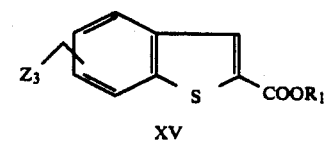  XV
CHART C
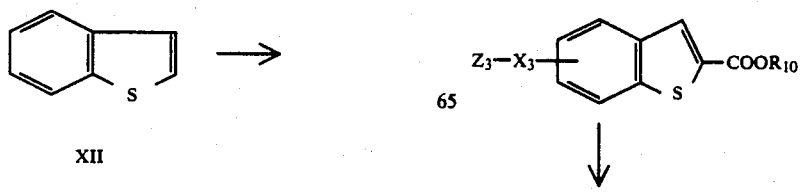  L

CHART C -continued

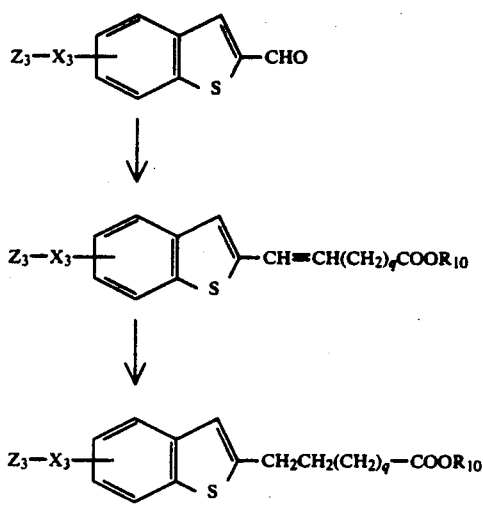

CHART D

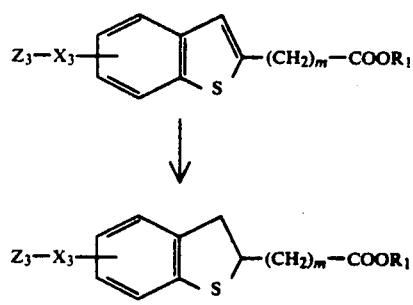

CHART E

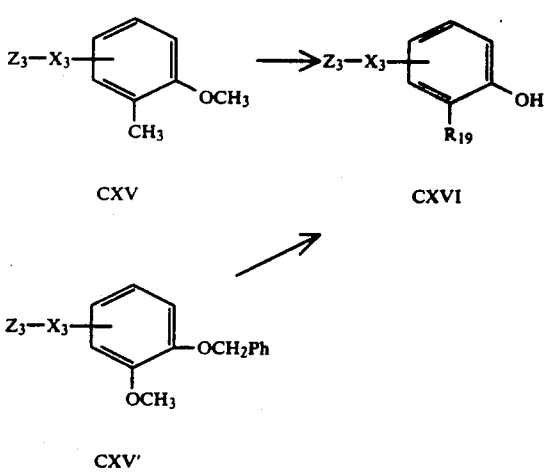

CHART F

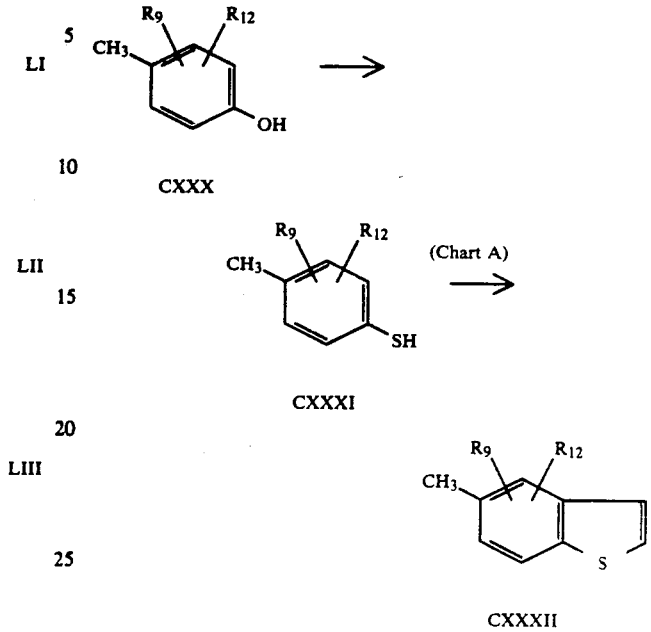

CHART G

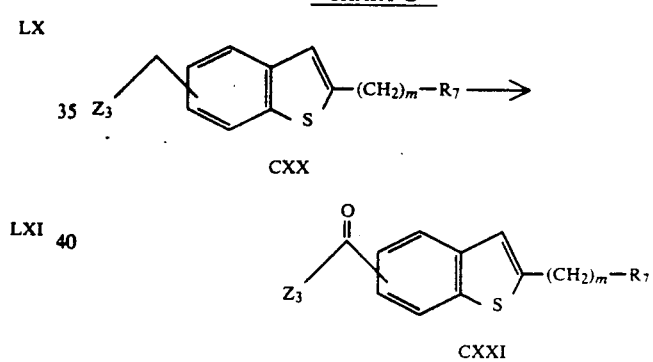

We claim:
1. A compound of the formula I

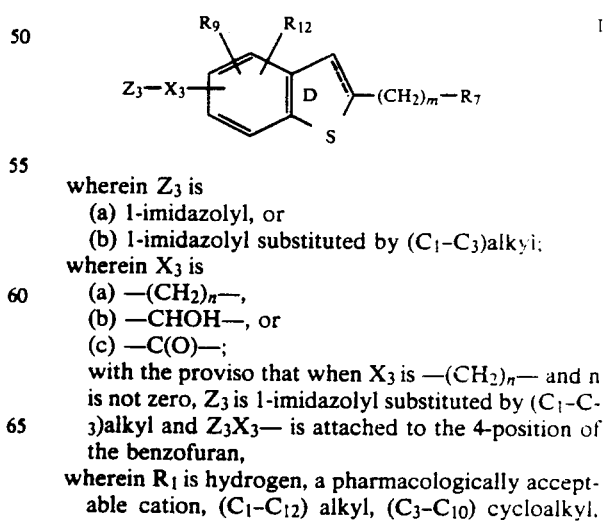

wherein $Z_3$ is
  (a) 1-imidazolyl, or
  (b) 1-imidazolyl substituted by $(C_1-C_3)$alkyl;
wherein $X_3$ is
  (a) $-(CH_2)_n-$,
  (b) $-CHOH-$, or
  (c) $-C(O)-$;
  with the proviso that when $X_3$ is $-(CH_2)_n-$ and n is not zero, $Z_3$ is 1-imidazolyl substituted by $(C_1-C_3)$alkyl and $Z_3X_3-$ is attached to the 4-position of the benzofuran,
wherein $R_1$ is hydrogen, a pharmacologically acceptable cation, $(C_1-C_{12})$ alkyl, $(C_3-C_{10})$ cycloalkyl, ($C_7$-$C_{12}$) aralkyl, phenyl, phenyl mono-, di-, or trisubstituted by chloro, ($C_1$-$C_3$) or alkyl, or phenyl para-substituted by
(a) —NHCO—$R_{25}$,
(b) —O—CO—$R_{26}$,
(c) —CO—$R_{24}$,
(d) —O—CO—(p—Ph)—$R_{27}$, or
(e) —CH=N—NH—CO—$NH_2$,
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein —(p—Ph) is 1,4-phenylene;
wherein $R_7$ is
(a) hydrogen,
(b) —$CH_2OH$,
(c) —$COOR_1$,
(d) —$CH_2N(R_4)_2$,
(e) —CN
(f) —$CON(R_4)_2$, or
(g) —C(O)—$R_4$;
wherein $R_4$ is
(a) hydrogen,
(b) ($C_1$-$C_4$)alkyl, or
(c) phenyl;
wherein $R_9$ and $R_{12}$ are the same or different and are
(a) hydrogen,
(b) ($C_1$-$C_4$)alkyl
(c) fluoro,
(d) chloro,
(e) bromo,
(f) —$OCH_3$, or,
(g) when taken together and attached to contiguous carbon atoms, —O—$CH_2$—O—;
wherein D represents a single or a double bond;
wherein m and n are the same or different and are the integers 0 to 4, inclusive; including, a pharmacologically acceptable acid addition salt thereof; and
when D represents a single bond, an enantiomer or a racemic mixture of enantiomers thereof.

2. A compound of claim 1, wherein D denotes a double bond, $X_3$ is —$(CH_2)_n$—, n is one or two, m is zero, $R_9$ and $R_{12}$ are hydrogen, and $R_7$ is —$COOR_1$.

* * * * *